United States Patent [19]

Vrolyk

[11] 4,020,696

[45] May 3, 1977

[54] HIGH PRESSURE, HIGH TEMPERATURE TRANSDUCER

[75] Inventor: John J. Vrolyk, Northridge, Calif.

[73] Assignee: Rockwell International Corporation, El Segundo, Calif.

[22] Filed: Feb. 23, 1976

[21] Appl. No.: 660,540

[52] U.S. Cl. .................................. 73/412; 73/86; 336/30; 73/398 R
[51] Int. Cl.² ................... G01L 7/04; G01N 17/00
[58] Field of Search ............ 73/411, 418, 420, 412, 73/413, 414, 415, 416, 417, 86, 398 R; 336/30

[56] References Cited

UNITED STATES PATENTS

| 2,823,543 | 2/1958 | Voss | 73/411 |
| 3,048,040 | 8/1962 | Pegram | 73/412 |

Primary Examiner—Donald O. Woodiel
Attorney, Agent, or Firm—L. Lee Humphries; Robert G. Upton

[57] ABSTRACT

The pressure measurement system utilizes two bourdon tubes with an active side connected to a test specimen and a reference side connected to an outside source. The tubes are attached to a single extensometer measuring relative displacement. The active side deflects when gases vent a specimen failure. The reference side is independently pressurized to a test pressure and provides a zero reference while providing a pressure calibration reference for the active side. The deflection noted by the active side at specimen failure is duplicated on the reference side by venting until an appropriate magnitude of pressure versus deflection is determined. In this way the pressure which existed inside the specimen prior to failure can be determined.

9 Claims, 3 Drawing Figures

HIGH PRESSURE, HIGH TEMPERATURE TRANSDUCER

The invention described herein was made in the performance of work under NASA contract No. NAS 8-27980 and is subjected to the provisions of Section 305 of the National Aeronautics and Space Act of 1958 (72 STAT 435; 42 USC2457).

BACKGROUND OF THE INVENTION

1. Field of the Invention

This invention is used primarily in the materials test area to determine fatigue life under various environmental conditions.

More particularly, this invention is directed to a means to measure high pressures during fatigue testing of candidate materials in a hydrogen-rich steam environment. The various candidate materials are subjected to vibratory strain oscillation as well as a high temperature, high pressure environment until they fail.

2. Description of the Prior Art

U.S. Pat. No. 3,095,745 describes a differential pressure instrument which is comprised essentially of two bourdon tubes, each having fixed ends and arranged so that the paths of movement of their free ends lie substantially along parallel lines spaced apart to accommodate a yoke or lever that is mechanically connected to a dial indicator or the like. The free end of one of the tubes moves along a substantially straight line in response to pressure differences, i.e., the motion of the free end thus being approximately rectalinear through a distance which is proportional to the change in pressure between the interior and the exterior of the tube. The tubes are oriented so that the line of movement of each is co-planar and parallel with the line of movement with the other, while the direction of each is opposite to the direction of movement of the other. The instant invention utilizes a pair of identical tubes configured in a substantially sine-like wave pattern, the direction of movement of each tube being the same as opposed to being opposite as is depicted in the foregoing patent. The purpose of the U.S. Pat. No. 3,095,745 patent is to measure the difference between pressure response of a pair of bourdon tubes, while the purpose of the present invention is to measure a single pressure and the differential aspect is only to allow temperature compensation and to facilitate calibration of the transducer without requiring its removal from a high temperature environment. Additionally, the instant invention has the advantage in that its use is particularly adaptable to limited space and high temperature hydrogen-rich steam environments and lends itself to the measure simultaneously of high pressure while being exposed to a high temperature hydrogen-rich steam environment. A further advantage is the use of multiple bourdon tubes connected in series each one added to an adjacent one, thus accommodating for large displacement while retaining high sensitivity. The foregoing patent does not incorporate these advantages.

In failure testing materials to determine fatigue life under a high temperature hydrogen-rich steam environment, it is necessary to measure the gas pressure inside a specimen containing approximately equal weights of hydrogen gas, and water vapor at pressures up to 7000 psia and temperatures up to 1400° F. If any part of the walls containing the gases should be allowed to cool down to the point where the water vapor condenses to form liquid droplets, most of the water would soon migrate to this particular area of the system, and the relative amount of water vapor in the gas would be depleted. Since the center of the specimen under test is at the highest temperature, the water vapor would migrate away from this region, the very place where the keeping of the proper proportions of hydrogen and water is of the greatest importance. Thus, in the system illustrated, the coolest region should be kept well above the condensation temperature of water. None of the prior art devices are adapted to perform in the foregoing environment. The instant invention avoids this problem because it has no direct internal cooling, therefore, a decided advantage over the prior art is realized.

SUMMARY OF THE INVENTION

A high pressure, high temperature transducer device of the type associated with fatigue testing of materials where the materials are subjected to vibratory strain oscillation, heated in a furnace and pressurized. The transducer consists of a pair of substantially identical parallel tubes, the tubes being tortiously deformed in a manner to assure that each tube will lengthen linearly when subjected to an internal pressure, each of the tubes are sealed at one end, the first active tube of the pair of tubes is connected internally to the interior of a specimen to be fatigue tested at the end opposite the sealed end while the second reference tube of the pair of tubes is connected to a reference pressure source at the end opposite the sealed end of the second tube. The sealed ends of the first and second tubes are connected to a means to measure relative displacement between the first and second tube when the specimen is heated, pressurized, and vibrated to failure.

The transducer consists of two parallel pieces of, for example, metal tubing each of which have been formed in an undulative or S-turn pattern. The identically shaped tubing pieces are laid side by side and the cutoff adjacent ends are sealed shut. The multiple undulations are really individual bourdon tubes connected in series, the ends connected to one another in a continuous chain. The opposite end of one tube is connected to a cavity of the specimen to be tested, while the corresponding end of the other tube is connected to an adjustable source of pressure comprised of, for example, an inert gas such as helium. When pressure is applied inside such tube, it tends to straighten out and this lengthening process can be utilized to indicate the magnitude of the pressure. Other phenomena, such as thermal expansion, will additionally cause lengthening; however, the parallel identical tube will compensate for this occurrence. A displacement measuring means which measures only the difference between the sealed ends of the two deformed tubes, rather than the absolute movement only, is provided. The relative displacement, for example, is measured with a linear, variable differential transformer which has the body fastened to the comparison tube and the core fastened to the specimen tube containing the test gases.

The active side of the two bourdon tubes deflects when gases vent at specimen failure. The reference side is independently pressurized to test pressure and provides a zero reference (thus accounting for creep effects) and provides a pressure calibration for the active side. The deflection noted by the active side at specimen failure is duplicated on the reference side by venting until the magnitude of pressure versus deflection is determined.

Thus, it is an object of this invention to provide a high pressure, high temperature transducer which will operate in a hydrogen-rich steam environment.

More specifically, it is an object of this invention to provide a high pressure, high temperature transducer that will operate in a hydrogen-rich steam environment when all components must be held above the steam saturation temperature during a specimen cycle test.

An advantage over the prior art is the placement of the test transducer within the furnace that is subjected to the hydrogen-rich steam environment.

Another advantage over the prior art is the use of parallel tubes having identical undulations or S-turn sections, one tube being connected to the test specimen and the other being provided solely as a reference tube.

Still another advantage over the prior art is that the pressure measurement system is changed from a gage readout to a bourdon tube deflection readout device.

Yet another advantage over the prior art is the use of a bourdon tube principle wherein multiple bourdon tubes are added together by connecting the ends of the bourdon tube one to another to form a continuous chain in series, thereby providing for large deflections and achieving a high degree of sensitivity.

The above noted objects and advantages of the present invention will be more fully understood upon a study of the following detailed description in conjunction with the detailed drawings.

DESCRIPTION OF THE PREFERRED EMBODIMENTS

Figure 2:
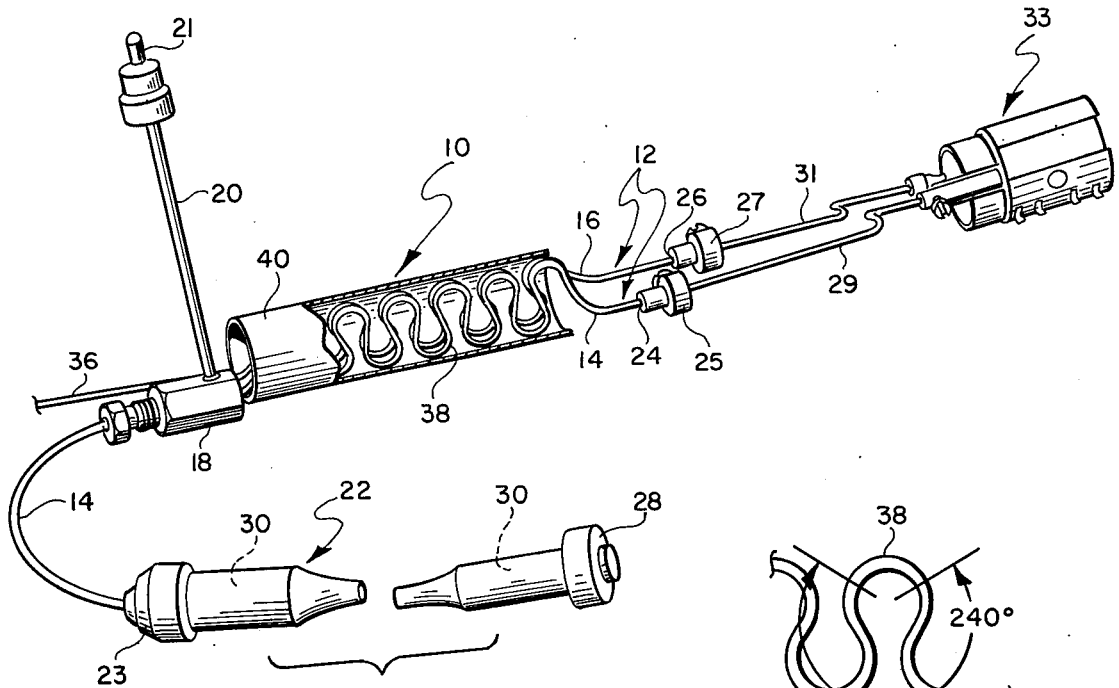
FIG. 2 is a partially cut away perspective view of the transducer.
Figure 1:
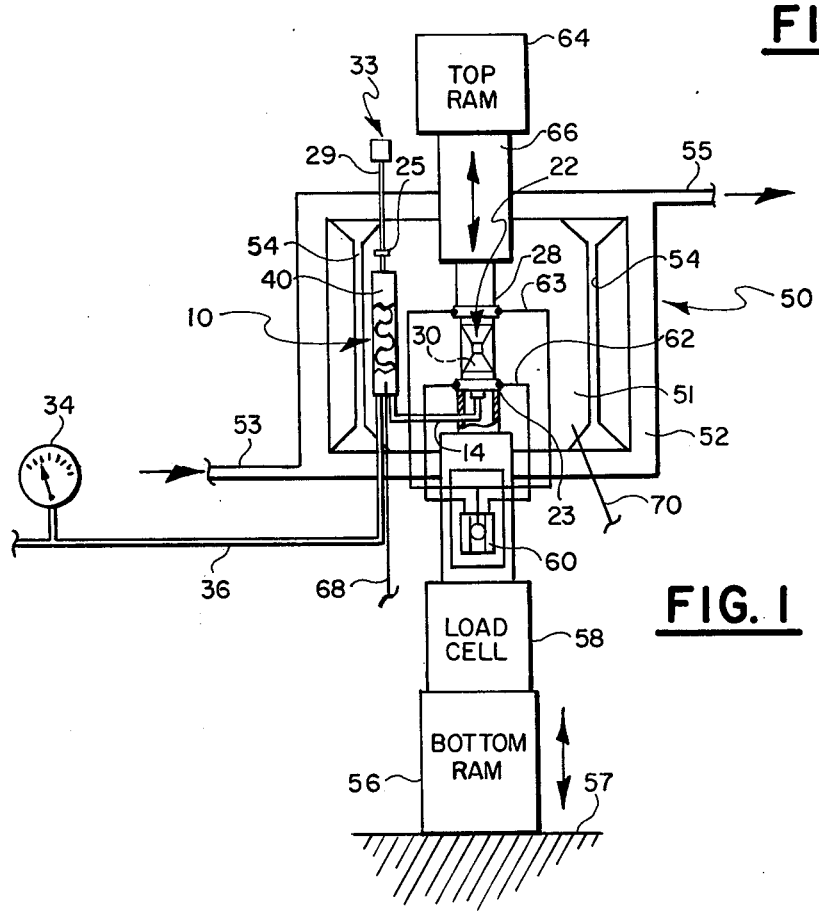
FIG. 1 is a schematic view of the transducer installed in a test environment.

Turning to the schematic as illustrated in FIG. 1, the transducer generally designated as 10 is installed within the interior 51 of quartz-lamp furnace generally designated as 50. Fatigue testing of candidate materials routinely use hollow metal specimens (22 of FIGS. 1 and 2). The hollow interior of the specimen 22 is normally subjected to a single gas environment such as hydrogen. The interior of the specimen may be subjected to hydrogen under, for example, 4000 psia while the quartz-lamp furnace 50 heats the specimen to, for example 1500° F. Normally once a particular gas environment is established, the specimen is isolated from the gas source to limit the quantity of gas vented at specimen failure. The specimen 22 is mechanically connected to a pair of rams 56 and 64 on the bottom and top respectively of each end of the specimen. The rams 56 and 64 alternately subject the specimen 22 to compressional and tensional loads. These oscillatory loads combined with heat and pressure subject the specimen to strains that will eventually catastrophically fail the specimen. A load cell 58 and a linear variable differential transformer, (LVDT) or extensometer 60 are connected between the bottom ram 56 and the end 23 of the specimen 22. End 28 of specimen 22 is connected to top ram 64 and the transition link 66. Rods 62 are connected between the LVDT and end 23, while another rod 63 is connected between the LVDT and the top 28 of specimen 22. The extensometer 60 then measures the amount of movement subjected to the specimen 22 by the rams 56 and 64 to control and calibrate not only the number of cycles per second that the specimen 22 is subjected to, but also the length of travel or strain that the rams push and pull the specimen.

The quartz-lamp furnace 50 is well known in the state of the art and it normally has a cooled liner around the furnace wherein water comes into the cavity 50 through conduit 53 and is circulated out through conduit 55, thus cooling the furnace. A purge of inert gas such as argon is fed into the interior 51 of the furnace 50 through conduit 70.

The transducer generally designated as 10 is installed within the interior 51 of the furnace 50. The transducer is generally comprised of a pair of parallel tubes, generally designated as 12 (FIG. 2), the pair of tubes 12 consist of an active side 14 and a reference side 60. The active tube 14 communicates with the interior 30 of the specimen 22 through end 23 of the specimen 22. Active tube 14 then is led into a coupling 18 and then into a series of, for example, undulations or S-bend turns for a predetermined length. The active tube 14 terminates in a sealed end 24 that is inserted within coupling 25. A mechanical link 29 then leads active tube 14 into a separate linear variable differential transformer 33. A reference tube 16 parallels active tube 14 and follows in an identical S-bend configuration along side (but not touching) the active tube 14. One end of the reference tube communicates with a source of inert gas under high pressure, such as helium which is in communication with a pressure gage 34 (FIG. 1) through conduit 36 into tube 16. The opposite end of tube 16 is sealed at end 26. The end 26 is inserted with coupling 27 which is connected to rod or link 31 which leads into LVDT 33. The pair of tubes generally designated as 12 where they are bent into S-turn configurations are protected by an outer shield 40. The coupling 18 allows water to be injected through end 21 of conduit 20 into the interior 30 of specimen 22 and of course into the interior of the active tube or conduit 14.

Normally, testing of sample type specimens in a test set up as configured in FIG. 1 encounters no problems where a single high-pressure environment is provided such as hydrogen. However, where water is introduced into the interior 30 of specimen 22 additional constraints are placed on the test system. All components exposed to the hydrogen and steam environment must now be above the steam saturation temperature or condensation will occur. Thus, the test specimen pressure indicator isolation valve and connecting plumbing as shown in FIG. 1 must be above the steam saturation temperature during a test. Where it is necessary to measure the gas pressure inside a specimen containing approximately equal weights of hydrogen gas and water vapor at pressures up to 7000 psia and temperatures up to 1400°–1500° F, if any part of the walls containing the gases should be allowed to cool down to a point where the water vapor condensed to form liquid droplets, all the water would soon migrate to this particular section of the specimen, the very place where the keeping of the proper portions of hydrogen and water is of the greatest importance, as heretofore described. Therefore it is obviously necessary to keep the coolest section of the test specimen 22 well above the condensation temperature of the water. Part of the problem is resolved by designing all test components to fit within the quartz-lamp furnace 50 as is indicated in FIG. 1.

A method was developed whereby measured amounts of high-temperature gas and water are sealed within the interior 30 of specimen 22 and the interior of the active transducer tube 14. Accurate volume measurements of the specimen and pressure transducer are necessary in order to calculate the quantities of water and hydrogen to be loaded within the specimen and active tube 14. After a measured amount of water is loaded through coupling 18 into the specimen 22, the specimen is then placed in a cold bath of, for example, alcohol and chilled with, for example a frozen carbon dioxide which freezes the water in the specimen. The transducer tube 14 attached to the specimen is then subjected to standard vacuum-pressurizing and pressurizing-vent-pressurizing cycle to remove any impurities within the specimen and active tube 14. The The water fill tube 20 is then welded shut as end 21 after the transducer and the specimen is subjected to vacuum-pressurizing and pressurizing-vent-pressurizing cycles to subject the interior of the specimen to the proper hydrogen-water mixture. The closed gas system wherein end 21 of conduit 20 and end 24 of conduit 14 is welded shut, assures that a controlled amount of hydrogen and water is subjected to the specimen prior to heating within the quartz-lamp furnace 50. The charging pressure of hydrogen and the quantity of water used are determined analytically. These calculations require accurate information on the specimen-transducer assembly volumes and target test conditions. Specimen (transducer) volume is determined by loading the specimen (transducer) with, for example, 2000 psi helium, then venting the specimen (transducer) to displace water in a beaker with millimeter graduations. This procedure is repeated five times and an average water displacement value determined. Calculations using the perfect gas law are made to determine the specimen and transducer volumes. With the transducer-specimen assembly volume known, the gas quantities required may be calculated once the hydrogen to steam mixture ratio is defined. To simplify the hydrogen to steam gas mixture ratio variable, a weight ratio of 1 (1) for all testing was chosen. This ratio approximates that found in a typical gas manifold. Defining the weight ratio of constituent gases allows calculation of hydrogen and steam gas partial pressures. The perfect gas law is used to determine the weights of gases needed for a test.

In operation the specimen 22 communicating with the active tube 14 along with reference tube 16 are placed within the interior 51 of the quartz-lamp furnace 50. Having previously preloaded the interior of the specimen and the active tube 14 with a mixture of hydrogen-water, the specimen 22 is now ready to be subjected to a test. The reference tube 16 is then subjected to a source of, for example, an inert gas such as helium to a high-pressure which will approximate the pressure that the specimen will be subjected to, for example, 7000 psia. The reference tube 16 then is pressurized to 7000 psia as is stabilized at this pressure. The quartz-lamp furnace is then started, reaching an interior temperature of approximately 1500° F which brings the hydrogen-steam mixture within cavity 30 of specimen 22 to approximately 7000 psia. The rams 56 and 64 are then set in motion and the specimen is subjected to vibratory strain oscillation while being in a high-temperature high-pressure environment.

A major problem in the liquid rocket engine field of technology is hydrogen embrittlement that the various metallic conduits are subjected to where hydrogen is one of the liquid fuels utilized. Eventually the specimen 22 fractures due to a combination of hydrogen embrittlement, heat and fatigue. When the specimen catastrophically fails and vents the pressure within the active tube 14, this tube then contracts due to the S-bend section of the tube, thus mechanically moving rod 29 which is connected to the LVDT 33. The pressure measurement system being essentially a bourdon tube deflection readout device allows for a direct reading of the physical movement of the bourdon tube 14 within the LVDT. The reference side being independently pressurized to test pressure provides a zero reference (thus accounting for creep effects) and provides a pressure calibration for the active side (tube 14). The deflection denoted by the active side at specimen failure is duplicated on the reference side by venting the reference bourdon tube 16 until an approximate magnitude of pressure versus deflection is determined. To extend the pressure transducer life, the bourdon tubes 14 and 16 are encased in a metal shield 40 and separately cooled somewhat by conduit 68 which feeds an inert gas such as argon into the interior of the shield 40. The gas circulating around the S-bend turns of the parallel tubes 14 and 16, thus the interior of the shield 40 is somewhat cooler tha the interior 51 of the quartz-lamp furnace 50. Incidently the interior 51 of the furnace is also subjected to argon purge through conduit 70 into the furnace to provide a safe environment for the test procedure, and to provide some cooling.

Figure 3:
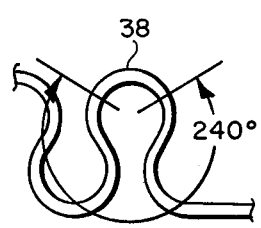
FIG. 3 is a section of the tube illustrating the undulating or S-bend configuration.

Turning to FIG. 3, the section of the bourdon tubes illustrated shows that each bend of the bourdon tube is bent through approximately a 240° arc, thus allowing for deflection of the parallel tubes 14 and 16.

Normally, a conventional bourdon tube is comprised of a single circular segment circumventing approximately 270° of arc. The ends of the tube either come toward each other upon evacuation or expand apart during pressurization. The present invention utilizes this principle by effectively connecting the ends of each bourdon tube in a series of undulations as stated above to form a continuous chain in series so that each undulation co-acts with an adjacent undulation to provide a combined output which is greater by a factor equal to the number of undulations in the series. The parallel bourdon tubes 14 and 16 are normally fabricated from stainless steel tubing.

It will of course be realized that various modifications can be made in the design and operation of the present invention without departing from the spirit thereof. Thus while the principal preferred construction and mode of operation of the invention have been explained in what is now considered to represent its best embodiment has been illustrated and described, it should be understood that within the scope of the appended claims the invention may be practiced otherwise than as specifically illustrated and described.

I claim:

1. A high pressure, high temperature transducer device of the type associated with fatigue testing of materials where said materials are subjected to vibratory strain oscillations, heated in a furnace and pressurized, said transducer comprising;

a pair of substantially identical parallel tubes, the tubes being tortiously deformed in a manner to assure that each tube will lengthen linearly when subjected to an internal pressure, each of said tubes are sealed at one end, the first active tube of said pair of tubes is connected internally to the interior of a specimen to be fatigue tested at the end opposite the sealed end while the second reference tube of said pair of tubes is connected to a reference pressure source at the end opposite the sealed end of said second tube, the sealed ends of said first and second tubes are connected to a means to measure relative displacement between said first and second tube when said specimen is vibrated, heated and pressurized to failure.

2. The invention as set forth in claim 1 wherein said pair of substantially identical parallel first and second tubes are enclosed in said heated furnace with said specimen.

3. The invention as set forth in claim 2 wherein said specimen is tested for hydrogen embrittlement by subjecting said first active tube and said specimen to a high temperature hydrogen-rich steam environment.

4. The invention as set forth in claim 1 wherein each of said first and second tubes are comprised for a continuous chain of bourdon tubes connected in series.

5. The invention as set forth in claim 1 wherein said first and second tubes are deformed into S-shaped undulating patterns.

6. The invention as set forth in claim 5 wherein each S-shaped bend in said tube is about 240°.

7. The invention as set forth in claim 1 wherein said reference pressure source is helium.

8. The invention as set forth in claim 1 wherein said tubes are stainless steel.

9. The invention as set forth in claim 1 wherein said means to measure displacement is a linear, variable, differential transformer.

* * * * *